United States Patent
Arnould

(10) Patent No.: US 7,331,937 B2
(45) Date of Patent: Feb. 19, 2008

(54) APPLICATOR FOR OBJECTS SUCH AS TAMPONS

(75) Inventor: Marc Arnould, Ohain (BE)

(73) Assignee: BirchBob International SA, La Hulpe (BE)

( * ) Notice: Subject to any disclaimer, the term of this patent is extended or adjusted under 35 U.S.C. 154(b) by 362 days.

(21) Appl. No.: 10/315,691

(22) Filed: Dec. 10, 2002

(65) Prior Publication Data

US 2003/0149392 A1 Aug. 7, 2003

(30) Foreign Application Priority Data

Feb. 5, 2002 (EP) ................................. 02100107

(51) Int. Cl.
*A61M 5/00* (2006.01)
(52) U.S. Cl. ........................ 604/111; 604/11; 604/12; 604/13; 604/14; 604/15
(58) Field of Classification Search ............ 604/11–15, 604/111
See application file for complete search history.

(56) References Cited

U.S. PATENT DOCUMENTS

| | | | | |
|---|---|---|---|---|
| 3,139,886 A | | 7/1964 | Tallman | 128/263 |
| 3,335,726 A | | 8/1967 | Maranto | 128/270 |
| 3,499,447 A | | 3/1970 | Mattes et al. | 128/263 |
| 4,211,225 A | * | 7/1980 | Sibalis | 604/385.18 |
| 4,286,594 A | * | 9/1981 | Cunningham | 604/15 |
| 4,318,404 A | * | 3/1982 | Cunningham | 604/12 |
| 4,413,986 A | * | 11/1983 | Jacobs | 604/14 |
| 4,421,504 A | | 12/1983 | Kline | 604/12 |
| 4,921,474 A | | 5/1990 | Suzuki et al. | 604/16 |
| 4,955,906 A | * | 9/1990 | Coggins et al. | 623/8 |
| 5,676,647 A | | 10/1997 | Cimber | 604/11 |
| 5,928,183 A | | 7/1999 | Fox et al. | 604/14 |

FOREIGN PATENT DOCUMENTS

| | | |
|---|---|---|
| DE | 37 39 163 A1 | 6/1989 |
| EP | 1014039 | 9/1983 |
| EP | 0349222 | 6/1989 |
| FR | 2002723 | 10/1969 |
| FR | 2546399 | 5/1983 |
| GB | 2056283 | 7/1980 |
| GB | 2153684 | 1/1985 |
| WO | WO 83/01741 | 5/1983 |

* cited by examiner

*Primary Examiner*—Tatyana Zalukaeva
*Assistant Examiner*—Ginger T. Chapman
(74) *Attorney, Agent, or Firm*—Womble Carlyle Sandridge & Rice, PLLC

(57) ABSTRACT

Applicator for inserting an object such as a tampon into a natural orifice of the human body, comprising the said object inserted in a tubular outer and a plunger intended to expel the said object such as a tampon from the tubular outer. The applicator comprises a flexible sleeve fixed concentrically to the outer, folded initially between the distal end of this outer and the object such as a tampon, the length of the deployed sleeve corresponding substantially to that of the object. The flexible sleeve deploys around the object such as a tampon when the latter leaves the outer under the effect of the plunger.

20 Claims, 2 Drawing Sheets

APPLICATOR FOR OBJECTS SUCH AS TAMPONS

This application claims convention priority from European patent application number EP-A-02100107, which has a filing date of Feb. 5, 2002. The specification and drawings of the European patent application are specifically incorporated herein by reference.

The invention relates to Applicator for introducing a solid object into a natural orifice of a human body.

The invention relates more specifically to tampons. Its principle can be applied also to the insertion and placement of other objects or devices in the field of medicine, such as probes, catheters, micro cameras, etc.

BACKGROUND OF THE INVENTION

One of the major disadvantages of tampons is the discomfort entailed in inserting them.

Although the development of Applicator made of a tube and of a plunger (known from EP 0 551 758) was a step forward in this area, there is nonetheless a great deal to be done to make this operation quick and painless.

One of the problems lies in the friction of the object such as a tampon after it has left the applicator, especially during menstruation when the mucous membranes are highly sensitive. A solution proposed i.a. in U.S. Pat. No. 3,499,447 and in GB 2 153 684 provides a short supple sleeve placed at the tip of the applicator so as to protect the distal end of the tampon at the moment of the intromission.

Numerous manufacturers have also attempted to develop solutions involving incorporating lubricants such as gels, either directly into the tampons (DE 3739163, GB 2 056 083) or into cavities or capsules incorporated into the applicators (U.S. Pat. No. 3,139,886; U.S. Pat. No. 4,421,504).

One of the disadvantages of the lubricants is that they may limit the absorption of the tampons. Furthermore, these lubricants, which give a greasy sensation to the touch, need to be released in situ, otherwise the applicator is unpleasant to handle.

Another approach consists in rounding the head of the applicator as much as possible. To this end, certain applicators have an ogee-shaped distal end, formed of petal cuts which splay outwards as the tampon passes (see EP 0 551 753). This solution, being more convenient, led to the abandonment of the supple sleeve cited above. One known problem is that these petals may trap the flesh when the applicator is withdrawn.

There has therefore been a search to develop Applicator which is easy to insert and which reduces the friction between the object such as a tampon and the walls of the orifice.

BRIEF DESCRIPTION OF THE INVENTION

The subject of the invention is an applicator for inserting an object into a natural orifice of the human body, comprising the said object inserted into a tubular outer and a plunger intended to expel the said object from the tubular outer. This applicator comprises a flexible sleeve fixed concentrically to the outer, between the distal end of this outer and the object. The flexible sleeve deploys around the object when the latter leaves the outer under the effect of the plunger. The length of the deployed sleeve corresponds to that of the object. The plunger is long enough to hold the object in place relative to the walls of the natural orifice while the object is disengaged from the sleeve by sliding the outer and the sleeve in the opposite direction to the direction of insertion.

According to one advantageous embodiment, the applicator is shaped to the female anatomy, the object to be inserted being a tampon.

The flexible sleeve may advantageously be fixed to the distal part of the outer, on the outside of the distal part of the outer or on the inside of the outer.

According to one advantageous embodiment, the flexible sleeve comprises a part arranged along the exterior wall of the outer.

The flexible sleeve is, according to one advantageous embodiment, initially open at its distal end.

According to another advantageous embodiment, the flexible sleeve is initially closed at its distal end and at that end comprises a part which is intended to rupture easily.

The material of the flexible sleeve preferably has a low coefficient of friction. Its exterior face may also be coated over at least part of its length with a lubricating substance. In this case, according to an advantageous embodiment, the distal part of the tampon is coated with an anti-absorbent substance.

According to a preferred embodiment, the plunger comprises two telescopic parts and a device for locking these two parts together.

According to an advantageous embodiment, the plunger comprises tactile marks, which allows its position to be assessed more precisely before withdrawing it.

One advantage of the invention is that it allows objects with relatively aggressive shapes or contours to be introduced into the body with a minimum of discomfort. This advantage is particularly pronounced in the case of the insertion of tampons during menstrual periods, which can be done painlessly.

Another advantage of the invention lies in the possibility of rectifying the position of the object before releasing it.

BRIEF DESCRIPTION OF THE DRAWINGS

Other specifics and advantages of the invention will become apparent from the description hereinbelow of some particular embodiments of the invention, reference being made to the appended drawings in which.

DETAILED DESCRIPTION OF THE DRAWINGS

Figure 1:
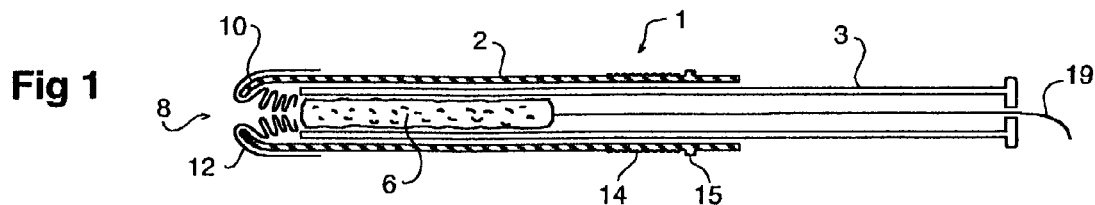
FIG. 1 is a view in axial section of a first form of an applicator according to the invention, in the case of a tampon.

The applicator 1 of FIG. 1, which is illustrated here in its role as a tampon applicator 1, has, in common with a conventional applicator, a tubular outer 2 and a plunger 3, here depicted in a position of rest, surrounding the object that is to be inserted, namely a tampon 6. The outer at its distal part 8 has an ogee shape obtained by cutting petals 10.

Unlike a conventional applicator, the present applicator comprises a sleeve 12 formed of a flexible membrane with a low coefficient of friction which is fixed concentrically to the outer 2. This sleeve 12 is fixed here to the outside of the tubular outer 2, covering its distal end 8, then is folded up inside the outer 2, between the distal end 8 and the tampon 6. The role of the sleeve 12 will be described with reference to FIGS. 2 to 4.

Figure 2:
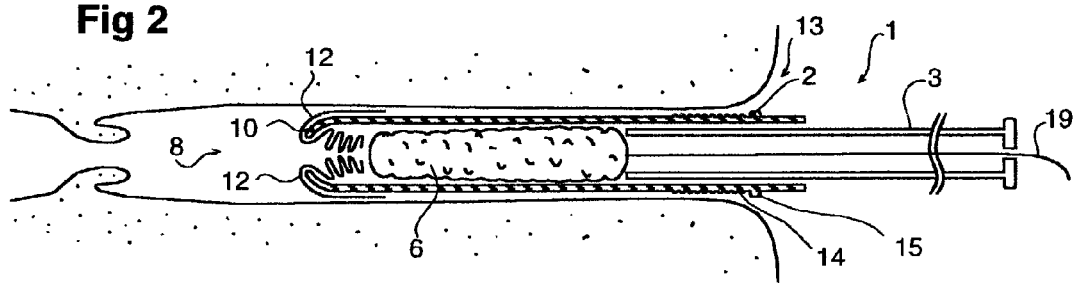
FIG. 2 is a schematic view in section of the applicator of FIG. 1, after priming and positioning.

FIG. 2 depicts the applicator 1 once the plunger 3 has been primed (that is to say pulled backwards and disengaged from the tampon 6) and the applicator 1 has been put in place in the ad hoc orifice 13, in this case the vagina 13.

Tactile marks 14 make it possible, in conjunction with a guard 15, to position the tubular outer 2 at the appropriate depth. It is actually essential that the tampon 6 should not be inserted too deeply and that it should, for example, remain short of the matrix 16.

Figure 3:
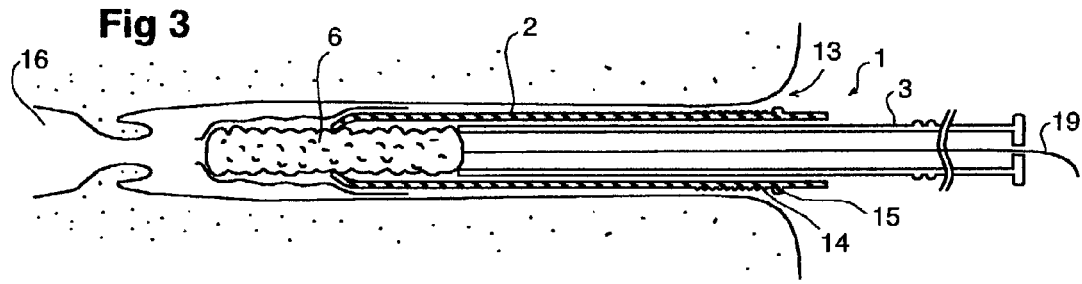
FIG. 3 is a schematic view in section of the applicator of FIG. 2, in a phase of inserting the tampon.

FIG. 3 shows the plunger 3 in the pushing-in phase; the tampon 6, pressed against the distal part 8 of the tubular outer 2, parts the petal cuts 10 and forces the sleeve 12 to deploy outwards. The membrane of the sleeve 12 which has a low coefficient of friction deploys in the vagina 13, surrounding the tampon 6 as it progresses, which can be achieved with very little effort.

Figure 4:
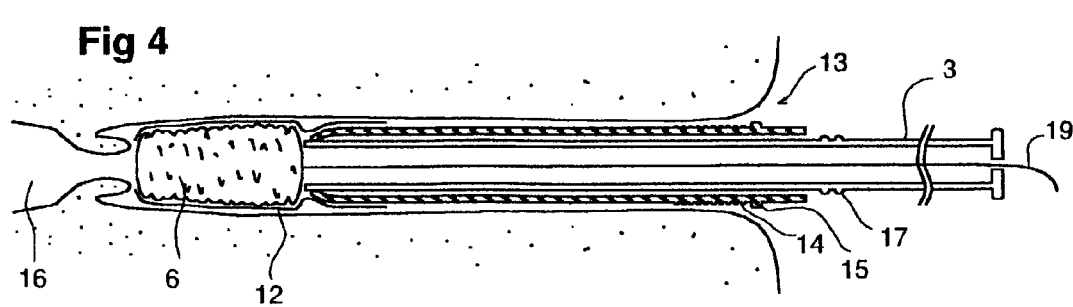
FIG. 4 is a schematic view in section of the applicator of FIG. 2, with the tampon inserted.

In FIG. 4, the tampon 6 has left the outer 2 and occupies its end position. It may be noted that the length of the sleeve 12 corresponds to that of the tampon 6. As the latter is still surrounded by the sleeve 12, it is still secured to the applicator 1, because of the low adhesion of the sleeve 12 to the wall of the vagina 13. It is therefore possible, at this stage, to rectify the position of the tampon 6 slightly (something which cannot be done with a conventional applicator). The presence of second tactile marks 17, formed on the plunger, makes it possible to check that this has been done correctly.

Figure 5:
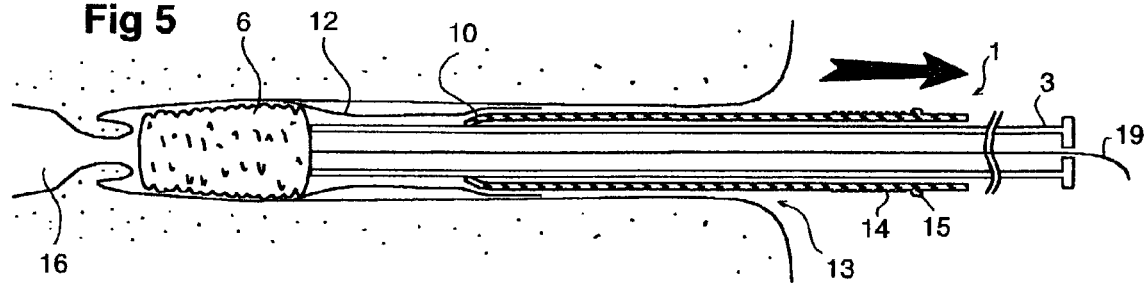
FIG. 5 is a schematic view in section of the applicator of FIG. 2, in the phase of withdrawing the outer and the sleeve.

FIG. 5 illustrates an additional phase specific to the invention, namely the disengagement of the tampon from the sleeve 12: the tubular outer 2 and the sleeve 12 are slid along the plunger 3 in a backwards movement while the tampon 6 is held firmly in place by the plunger 3. It will be noted that the latter is longer than in a conventional applicator. The assembly [plunger 3+outer 2 and sleeve 12] can be withdrawn without problem once the tampon 6 has been completely disengaged.

The sleeve 12 is depicted in FIGS. 1 to 4 in the form of a tubular casing open at both ends. As its proximal end is secured to the outer 2, it goes without saying that it is just as possible to provide a sleeve which is initially "closed" at its distal end, either by a cap which has lines of weakness or by pleating held in place by one or two spot welds which are easily torn to allow the tampon 6 to pass.

The material used to make the sleeve 12 may be extremely thin, of the order of that used for condoms. The sleeve needs to have good flexibility and slide readily, which results in a maximum amount of gentleness against the wall of the vagina, but it does not need also to have exceptional mechanical properties. Indeed all that is required is for its diameter to be slightly greater than that of the tampon 6 so as to allow sliding without force and without jerkiness. It is possible to choose a material which intrinsically has a low coefficient of friction against the wall of the vagina 13 or to opt for a material which is coated over all or part of its external surface with a lubricant known from other applications. It has been checked experimentally that contact between the tampon 6 and the surface of a sleeve 12 coated with lubricant has virtually no effect on the absorption of the tampon 6. In any event, contact is only with the distal part of the tampon 6. In certain cases, it may, however, be envisaged for the tip of the tampon 6 to be soaked in a product that neutralizes any interactive effect.

It is clearly apparent from FIG. 4 that the plunger 3 of the present applicator 1 is longer than the plunger of a normal applicator. This is because it has to be longer than the sum of the lengths of the tubular outer 2 and of the deployed sleeve 12 and allow the disengagement described in FIG. 5. By adjusting the relative lengths of the various parts, it can, however, be seen that the elongation by comparison with a conventional plastic applicator is barely 5.5 cm, and just a few mm with respect to a coated cardboard applicator. The length of the cord 19 for removing the tampon 6 is obviously adjusted to suit this feature.

Figure 6:
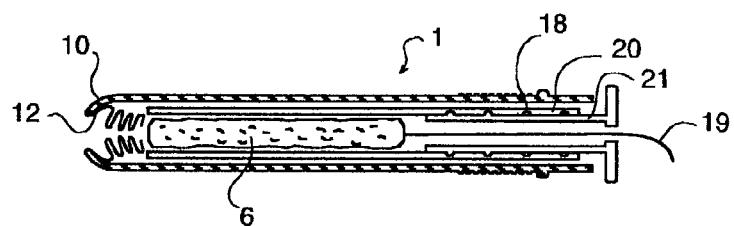
FIG. 6 is a view in axial section of another embodiment of the invention with telescopic plunger.

As additional bulk may detract from the discreet nature of the applicator 1 as regards its use for tampons 6, attempts were made to produce a particularly compact version. FIG. 6 shows Applicator equipped with a telescopic plunger 3. Stops 18 or a quarter-turn lock allow the two elements 20, 21 of the plunger 3 to be locked together when the applicator 1 is primed. FIG. 6 also depicts another possibility for the attachment of the sleeve 12, which in this instance is bonded to the inside of the walls of the outer 2.

Figure 8:
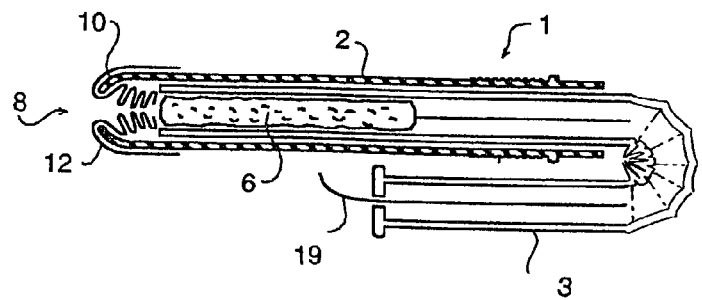
FIG. 8 is a view in axial section of another embodiment of the invention with a foldable plunger.

FIG. 8 describes an alternative possibility to reduce the overall length of the applicator. In this case, the plunger comprises two folding parts. The proximal end of the plunger, normally turned down along the outer 2 is set upright prior to the insertion.

Figure 7:
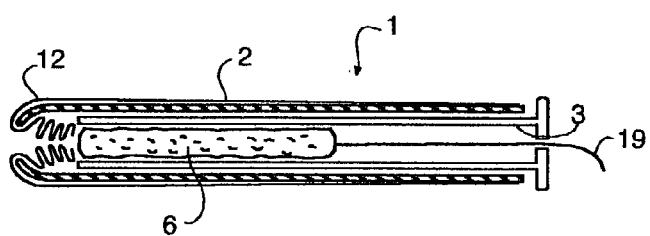
FIG. 7 is a schematic view of another embodiment of the invention.

FIG. 7 shows another advantageous possible embodiment of the present applicator 1: the sleeve 12 here is bonded or welded over the entirety of the outer 2, which allows the use, for the outer 2, of material which has a poorer finish while at the same time improving insertion comfort. The possible presence of a lubricant is, in this case, limited to the folded-up part of the sleeve 12.

It will be noted that the presence of the sleeve 12, whether fixed to the inside or the outside of the outer 2, makes it possible to avoid any pinching of the flesh by any petal cuts 10.

Although the applicator 1 has been described in a particular context of the insertion of a tampon, it goes without saying that its principle can also be applied to the insertion and placement of other objects or devices in the field of medicine, such as probes, catheters, micro cameras, certain types of drug, etc, and in general to any type of element which may prove aggressive to the wall of an organ.

I claim:

1. Applicator for inserting a tampon into a natural orifice of a human body, the applicator being shaped to the female anatomy, comprising:

the tampon having a length, a proximal end, a distal end and being inserted into a tubular outer, a plunger intended to expel the tampon from the tubular outer, and a flexible sleeve fixed concentrically to the outer, between the distal end of the outer and the tampon;

wherein the sleeve deploys around the tampon within the orifice and surrounds the entire length of the tampon, including the distal end of the tampon, when the tampon is expelled from the outer under the effect of the plunger, the deployed sleeve having a length at least equal to the length of the tampon to surround the tampon fully until insertion into the natural orifice by the plunger is complete, and wherein the length of the plunger corresponds at least to the sum of the length of the tubular outer and the deployed sleeve, the length of the plunger enabling the tampon to be held in place relative to the wall of the natural orifice while the tampon is disengaged from the sleeve by sliding the outer and the sleeve in the opposite direction to the direction of insertion.

2. Applicator according to claim 1, wherein the flexible sleeve is fixed to the distal end of the outer.

3. Applicator according to claim 2, wherein the flexible sleeve is fixed on the outside of the distal end of the outer.

4. Applicator according to claim 2, wherein the flexible sleeve is fixed on the inside of the outer.

5. Applicator according to claim 1, wherein the flexible sleeve comprises a part arranged concentrically to the exterior wall of the distal end of the outer.

6. Applicator according to claim 1, being shaped to the female anatomy.

7. Applicator according to claim 6, wherein the flexible sleeve comprises a part arranged along the exterior wall of the outer.

8. Applicator according to claim 6, wherein the plunger comprises two telescopic parts and a device for locking these two parts together in deployed condition.

9. Applicator according to claim 6, wherein the plunger comprises tactile marks.

10. Applicator according to claim 6 wherein the plunger comprises a folding proximal part.

11. Applicator according to claim 1, wherein the flexible sleeve is fixed to the distal end of the outer.

12. Applicator according to claim 11, wherein the flexible sleeve is fixed on the outside of the distal end of the outer.

13. Applicator according to claim 11, wherein the flexible sleeve is fixed on the inside of the outer.

14. Applicator according to claim 1, wherein the material of the flexible sleeve has a low coefficient of friction.

15. Applicator according to claim 1, wherein the exterior face of the flexible sleeve is coated over at least part of its length with a lubricating substance.

16. Applicator according to claim 1, wherein the distal end of the tampon is coated with an anti-absorbent substance.

17. An applicator for inserting a tampon into a natural orifice of a female human body, the applicator comprising:
  a tubular outer housing the tampon; the tampon having a proximal end and a distal end;
  a plunger disposed at the proximal end of the tampon within the tubular outer; and
  a flexible sleeve fixed concentrically to the outer;
  wherein the sleeve deploys around and surrounds the distal end of the tampon as the plunger expels the tampon from the tubular outer, the sleeve surrounding the distal end of the tampon at least until the plunger has expelled the proximal end of the tampon from the outer.

18. The applicator of claim 17 wherein withdrawal of the tubular outer from the orifice causes the flexible sleeve to withdraw from the distal end of the tampon and leaves the tampon in place within the orifice.

19. An applicator for inserting a tampon into a natural orifice of a female human body, the applicator comprising:
  a tubular outer housing the tampon; the tampon having a proximal end and a distal end;
  a plunger disposed at the proximal end of the tampon within the tubular outer; and
  a flexible sleeve fixed concentrically to the outer;
  wherein the sleeve deploys around and surrounds the tampon as the plunger expels the tampon from the tubular outer, the sleeve surrounding the distal end of the tampon within the orifice until insertion by the plunger is complete.

20. An applicator for inserting a tampon into an orifice, the applicator comprising:
  a tubular outer housing the tampon prior to insertion;
  a plunger in the tubular outer for selectively ejecting the tampon from the tubular outer and into the orifice;
  a flexible sleeve fixed concentrically to the tubular outer adjacent the tampon;
  the flexible sleeve deploying around the tampon within the orifice as the tampon is ejected from the tubular outer and surrounding the tampon completely when the tampon has been fully ejected from the tubular outer and positioned within the orifice;
  withdrawal of the tubular outer from the orifice causing the flexible sleeve to withdraw from around the tampon leaving the tampon in place within the orifice.

* * * * *